(12) United States Patent
Hara et al.

(10) Patent No.: US 7,351,863 B2
(45) Date of Patent: *Apr. 1, 2008

(54) METHOD OF FLUORINATION

(75) Inventors: Shoji Hara, Hokkaido (JP); Tsuyoshi Fukuhara, Hokkaido (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 90 days.

This patent is subject to a terminal disclaimer.

(21) Appl. No.: 10/537,437

(22) PCT Filed: Dec. 1, 2003

(86) PCT No.: PCT/JP03/15336

§ 371 (c)(1),
(2), (4) Date: Jun. 3, 2005

(87) PCT Pub. No.: WO2004/050676

PCT Pub. Date: Jun. 17, 2004

(65) Prior Publication Data

US 2006/0014972 A1 Jan. 19, 2006

(30) Foreign Application Priority Data

Dec. 4, 2002 (JP) ............................. 2002-352968
Dec. 10, 2002 (JP) ............................. 2002-358249

(51) Int. Cl.
C07C 211/27 (2006.01)
C07H 5/02 (2006.01)
C07H 1/00 (2006.01)

(52) U.S. Cl. ...................................... 564/366; 536/124
(58) Field of Classification Search ................ 536/124; 564/366

See application file for complete search history.

(56) References Cited

U.S. PATENT DOCUMENTS 3,101,357 A 8/1963 Bowers
7,019,173 B2 * 3/2006 Hidaka et al. ............... 564/384

FOREIGN PATENT DOCUMENTS

| EP | 1 172 369 A1 | 1/2002 |
| JP | 2003-064034 | 3/2003 |
| WO | WO 97/41083 | 11/1997 |
| WO | WO 00/58240 | 10/2000 |
| WO | WO 01/02320 A1 | 1/2001 |

OTHER PUBLICATIONS

U.S. Appl. No. 10/591,698, filed Sep. 2006, Hara, Shoji.*
Dmowski et al., Dialkyl alpha,alpha-difluorobenzylamines and dialkyl(trifluoromethyl)-amines—Novel Fluorinating Reagents Journal of Fluorine Chemistry (1983) vol. 23, pp. 219-228.*
Chirakal et al., "Base-mediated Decomposition of a Mannose Triflate During the Synthesis of 2-Deoxy-2-18F-fluoro-D-glucose" Applied radiation and isotopes (1995) vol. 46, No. 3, pp. 149-155.*
Dmowski et al., "Reactions of N,N-dialkylbenzamides with Sulfur Tetrafluoride, Formation of Dlalkyl-alpha,alpha-Difluorobenzylamines" Polish Journal of Chemistry (1982) vol. 56, pp. 1369-1378.*
Journal of Flourine Chemisitry vol. 23, Sep. 3, 1983 ISSN 0021139 pp. 219-228.
Tetrahedron Letters, vol. 27, No. 3, pp. 279-282, 1986.
Edited by CSJ: The Chemical Society of Japan, "Shin Jikken Kagaku Koza 14 Yuki Kagobutsu No. Gosel to Han'no [1]", (publisher Maruzen Co., Ltd.), 1977, pp. 308-331.

* cited by examiner

Primary Examiner—Shaojia Anna Jiang
Assistant Examiner—Eric S Olson
(74) Attorney, Agent, or Firm—Antonelli, Terry, Stout & Kraus, LLP.

(57) ABSTRACT

A method of fluorination comprising reacting monosaccharides, oligosaccharides, polysaccharides, composite saccharides formed by bonding of these saccharides with proteins and lipids and saccharides having polyalcohols, aldehydes, ketones and acids of the polyalcohols, and derivatives and condensates of these compounds with a fluorinating agent represented by general formula (I) thermally or under irradiation with microwave or an electromagnetic wave having a wavelength around the microwave region. In accordance with the method, the fluorination at a selected position can be conducted safely at a temperature in the range of 150 to 200° C. where the reaction is difficult in accordance with conventional methods. The above method comprising the irradiation with microwave or an electromagnetic wave having a wavelength around the microwave region can be applied to substrates other than saccharides

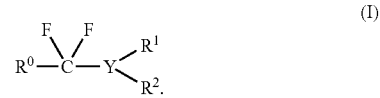

(I)

11 Claims, No Drawings

METHOD OF FLUORINATION

This application is a national stage application of PCT/JP03/15336, filed Dec. 1, 2003, which claims priority to foreign applications JP2002-352968, filed Dec. 4, 2002, and JP2002-358249, filed Dec. 10, 2002.

TECHNICAL FIELD

The present invention relates to a method of fluorination. More particularly, the present invention relates to a method of selectively fluorinating saccharides useful as the functional chemicals such as materials for drugs, cosmetics and healthy foods, and a method of efficiently fluorinating a substrate by bringing the substrate into reaction with a fluorinating agent under irradiation with microwave or electromagnetic wave having a wavelength around the microwave region.

BACKGROUND ART

Compounds having fluorine have been attracting attention in various fields such as the medical field and the field of electronic materials since the unique property derived from fluorine atom leads to exhibition of various useful functions, and the compounds have numerous applications. Therefore, various methods of effectively introducing fluorine atom into substrates have been studied. Examples of the widely known methods include the method of direct fluorination described in Japanese Patent Application Laid-Open No. Showa 53(1978)-1827; the so-called method of halogen exchange described in Yuki Gosei Kagaku (Organic Synthetic Chemistry), volume 47, page 258 (1999), in which a halogen atom in a compound having the halogen atom is exchanged with fluorine atom using HF or an alkali metal salt of fluorine such as KF; the method using hydrogen fluoride and a base such as pyridine and triethylamine; the method using a hypervalent iodine such as $IF_5$; the method using a specific fluorinating agent such as $SF_4$, DAST and a fluoroalkylamine, examples of which include the Yarovenko reagent; and the method of electrolytic fluorination (Chemistry of Organic Fluorine Compounds II, Monograph, American Chemical Society, 1995, page 187).

However, among the conventional methods, the methods of fluorination using fluorine gas, $SF_4$ or DAST have a great problem with respect to safety of the reaction. The method using a nucleophilic fluorinating agent which can introduce fluorine atom conveniently and safely such as a combination of HF and a base is frequently conducted in early stages of research and development since distillation is made possible by adjusting the number of the HF molecule coordinated to the base, and glass wares can be used without the possibility of corrosion. This method is described in references (Journal fur practische Chemie Chemiker-Zeitung, 338 (1996), pages 99 to 113; G. A. Olah, Synthetic Fluorine Chemistry, chapter 8, 1992, John Wiley).

Examples of the method using a nucleophilic fluorinating agent include fluorination of sugars by the halogen-fluorine exchange such as the halogen-fluorine exchange of a compound having a halogen atom activated by carbonyl group at the α-position, the halogen-fluorine exchange of trichloropyrimidine and the halogen-fluorine exchange of a sugar triflate; synthesis of fluoroethanols by ring-opening fluorination of oxirane compounds (formation of a fluorohydrin); formation of halofluoro group or fluorosulfenyl group in unsaturated compounds; synthesis of fluorobenzene by fluorination accompanied with removal of diazo group; gem-difluorination of 1,3-dithiolanes and hydrazones; and the reaction of removing protective group of silyl ethers.

However, although the easy formation of free HF can be suppressed so that the safety of the complex compound of HF and a base is enhanced, drawbacks arise in that the formation of the fluorine anion having the nucleophilicity becomes difficult, and the reactivity is small. Therefore, severe reaction conditions are necessary to obtain an excellent result of the reaction, and it is often difficult that the desired reaction proceeds. Moreover, from the standpoint of the industrial application, improvement is necessary for completing the reaction at a low temperature in a short time so that the energy cost is reduced.

It is the actual situation that the other fluorinating agents are expensive and cannot be handled easily. Among the above methods, the method of using a specific compound having fluorine atom as the fluorinating agent is frequently used in the early stage of research and development on drugs and functional materials since fluorine atom can be introduced relatively easily. However, as described above, the conventional technology of fluorination is not satisfactory for making the desired fluorination proceed selectively, efficiently and safely.

Recently, various attempts have been made to improve the selectivity and the activity of the reaction. Examples of the attempt include the acceleration of the reaction using microwave. Since microwave does not have energy sufficient for starting a reaction, the application of microwave to chemical reactions is heretofore rarely conducted. Recently, a study showing that the activity and the selectivity of a reaction is improved by irradiation with microwave has been reported. This report is attracting attention since the result cannot be explained by the simple acceleration of the reaction by heating (Journal of Physical Organic Chemistry, 2000 (13), 579-586). However, the attempts on the application of microwave to the fluorination are scarce. For example, no reports can be found except the application to the Schieman reaction (Japanese Patent Application (as a national phase under PCT) Laid-Open No. Heisei 12(2000)-59384).

As for saccharides, a wide range of application and development are expected since saccharides play important roles in the activities of the life such as the communication between cells and the mechanism of immunity as the energy source and as the sugar chain in proteins and have the ability of forming organs such as skins and bones. For example, chitosan, which is a high order condensate having a repeating unit of glucosamine and is produced by hydrolysis or fermentation of crustaceans or glucose as the material, is used as an additive, an antiseptic or a pet food in the field of foods and as an artificial skin, a stitching thread, a membrane for artificial dialysis and a film for controlled release in the field of medical treatments. Chitosan is also used in the field of the drug as an anticancer agent, an immunostimulator, an agent for suppressing blood glucose elevation and an agent for suppressing cholesterol absorption, in the field of the agriculture as an agent for soil amelioration, an antivirus agent and an insecticide, in the field of industry as soap, a hair tonic, a cosmetic and a tooth paste, and in the field of the environment as an agent for trapping waste fluids and an agent for treating heavy metals and waste water.

As described above, as the application of saccharides, the development of products having useful functions in the fields of foods, drugs, medical treatments, agriculture, industry and environment is promoted by bonding specific monosaccharides in higher orders or by introducing amino group, acetyl group or fluorine atom into saccharides.

In particular, fluorinated sugars obtained by fluorinating saccharides exhibiting excellent adaptability to the human body are actively studied for application as the anticancer agent and an immunosuppressant. Examples of the method of fluorination used for this purpose include the direct fluorination with the fluorine gas, the method of halogen-fluorine exchange, the method using hydrogen fluoride and a base such as pyridine and triethylamine, and the method using a fluorinating agent such as $IF_5$, $SF_4$, DAST and the Yarovenko reagent.

However, the introduction of fluorine atom into a specific position of a saccharide is often difficult since a saccharide has a plurality of active groups such as hydroxyl groups. For example, it is known that, when methyl 2,3-0-isopropylidene-β-D-ribofuranoside is fluorinated with DAST, 2,3-0-isopropylidene-5-0-methyl-β-D-ribofuranosyl fluoride which is a product of rearrangement is obtained, but the fluorination of hydroxyl group as the object reaction does not proceed. It is also known that the object reaction does not proceed when the combination of HF and a base which is a convenient fluorinating agent such as the HF-pyridine complex compound and the HF-triethylamine complex compound is used. When an agent having a greater acidity is used to promote the reaction, side reactions such as scission of the protective group take place.

When fluorine gas having a greater reactivity is used, the selective introduction of fluorine is impossible. To obtain the object compound, it is necessary that the halogenation be conducted using another halogen having a smaller reactivity, and then the halogen-fluorine exchange be conducted.

As described above, it is very difficult that a specific position of a saccharide is easily fluorinated without affecting the protective group in accordance with the conventional technology.

The present invention has an object of overcoming the above problems and providing a method of making the fluorination of a desired substrate proceed highly selectively, efficiently and safely, and to provide a method of fluorinating a specific position of a saccharide selectively without affecting a protective group at a temperature within a wide range safely and easily.

DISCLOSURE OF THE INVENTION

As the result of intensive studies by the present inventors to overcome the above problems, it was found that, when monosaccharides, oligosaccharides, polysaccharides, composite saccharides formed by bonding of these saccharides with proteins and lipids and saccharides having polyalcohols, aldehydes, ketones and acids of the polyalcohols, and derivatives and condensates of these compounds were brought into reaction with a specific fluorinating agent thermally or under irradiation with microwave or an electromagnetic wave having a wavelength around the microwave region, the fluorination could be conducted selectively at a specific position safely at a temperature in the range of 150 to 200° C. where the reaction was heretofore difficult.

It was also found by the present inventors that the method of irradiating with microwave or electromagnetic wave having a wavelength around the microwave region could be applied to substrates other than the saccharides, and the fluorination at a specific position which had been difficult in accordance with the conventional technology proceeded highly selectively, efficiently in a short time and safely by conducting the reaction using other fluorinating agents under irradiation with microwave.

The present invention provides:

(1) A method of fluorination which comprises fluorinating a saccharide using a fluorinating agent represented by general formula (I):

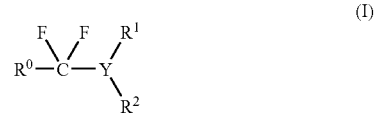

wherein Y represents nitrogen atom or phosphorus atom, $R^0$, $R^1$ and $R^2$ represent hydrogen atom or an alkyl or aryl group which may have substituents, the atom and the groups represented by $R^0$, $R^1$ and $R^2$ may be a same with or different from each other, and two or three of the groups represented by $R^0$, $R^1$ and $R^2$ may be bonded to each other to form a ring;

(2) A method of fluorination described above in (1), wherein, in general formula (I), Y represents nitrogen atom, $R^0$ represents 3-methylphenyl group or 2-methoxyphenyl group, and $R^1$ and $R^2$ represent ethyl group;

(3) A method of fluorination described above in any one of (1) and (2), wherein the saccharide is fluorinated by a thermal reaction;

(4) A method of fluorination which comprises fluorinating a substrate by bringing the substrate and a fluorinating agent into reaction with each other under irradiation with at least one of microwave and electromagnetic wave having a wavelength around a microwave region.

(5) A method of fluorination described above in (4), wherein the fluorinating agent is a compound represented by general formula (II):

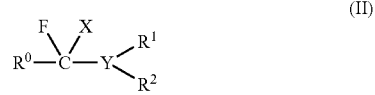

wherein Y represents nitrogen atom or phosphorus atom, X represents hydrogen atom or a halogen atom, $R^0$, $R^1$ and $R^2$ represent hydrogen atom or an alkyl or aryl group which may have substituents, the atom and the groups represented by $R^0$, $R^1$ and $R^2$ may be a same with or different from each other, and two or three of the groups represented by $R^0$, $R^1$ and $R^2$ may be bonded to each other to form a ring;

(6) A method of fluorination described above in (5), wherein the fluorinating agent is a compound represented by general formula (III):

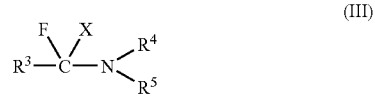

wherein $R^3$, $R^4$ and $R^5$ each independently represent an alkyl or aryl group which may have substituents, X represents hydrogen atom or a halogen atom, and two or three of the groups represented by $R^3$, $R^4$ and $R^5$ may be bonded to each other to form a cyclic structure;

(7) A method of fluorination described above in any one of (5) and (6), wherein the substrate is an organic compound having at least one atom selected from oxygen atom, nitrogen atom and sulfur atom;

(8) A method of fluorination described above in (4), wherein the fluorinating agent is a complex compound comprising HF and a base; and (9) A method of fluorination described above in (8), wherein the substrate is a compound having hydrogen atom activated by a substituent at an α position, a β-position or a γ-position, a silyl ether compound, a compound having an unsaturated group, hydroxyl group, a halogeno group, amino group, diazo group, triazeno group or isocyano group as a functional group, or a cyclic compound having three-membered or greater ring which may have heteroatoms.

THE MOST PREFERRED EMBODIMENT TO CARRY OUT THE INVENTION

As the saccharide used in the present invention, polyalcohols and other substances can be used. Examples of the other substances include monosaccharides such as glucose, fucose, N-acetylglucosamine, N-acetylgalactosamine, N-acetylneuraminic acid, erythrose, threose, ribose, arabinose, xylose, arose, lyxose, altrose, mannose, gulose, idose, galactose, talose, psicose, furctose, sorbose, tagatose, unsaturated sugars having an unsaturated bond such as hexaenose, branched sugars such as apiose, and derivative of sugars such as deoxy sugars, amino sugars, thio sugars, condensed sugars and anhydrides of monosaccharides; oligosaccharides, including disaccharides, comprising two to several monosaccharides bonded through the glycoside bond such as maltose, cane sugar and lactose; polysaccharides such as starch, glycogen and cellulose; composite saccharides obtained by bonding of these saccharides with proteins and lipids; and nucleosides, oligonucleosides, ribonucleic acid and deoxyribonucleic acid which are obtained by bonding of these saccharides with bases of nucleic acids.

The fluorinating agent used for fluorination of the above saccharides is a compound represented by the following general formula (I):

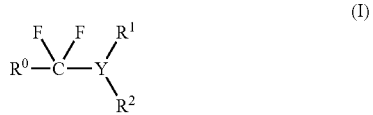

(I)

In general formula (I), $R^0$, $R^1$ and $R^2$ represent hydrogen atom or an alkyl or aryl group which may have substituents, the atom and the groups represented by $R^0$, $R^1$ and $R^2$ may be the same with or different from each other, and two or three of the groups represented by $R^0$, $R^1$ and $R^2$ may be bonded to each other to form a ring.

As the alkyl group, saturated and unsaturated aliphatic and alicyclic alkyl groups having 1 to 32 carbon atoms are preferable. Examples of the alkyl group include methyl group, ethyl group, propyl group, isopropyl group, butyl group, isobutyl group, t-butyl group, pentyl group, hexyl group, heptyl group, octyl group, 2-ethylhexyl group, nonyl group, decyl group, cyclohexyl group, cyclooctyl group, decalyl group, norbornyl group, bicyclohexyl group, adamantyl group, isomers of these groups, hydroxymethyl group, hydroxyethyl group, hydroxypropyl group and hydroxybutyl group.

Examples of the aryl group include aromatic aryl groups such as phenyl group, o-tolyl group, m-tolyl group, p-tolyl group, o-xylyl group, m-xylyl group, p-xylyl group, dimethylphenyl group, isomers of dimethylphenyl group having methyl group at different positions, cumyl group, mesityl group, trimethylphenyl group, hydroxyphenyl group, methoxyphenyl group, isomers of methoxyphenyl group having methoxyl group at different positions, naphthyl group, methylnaphthyl group, dimethylnaphthyl group, hydroxynaphthyl group, biphenyl group, tetralyl group, terphenyl group, anthryl group, benzothienyl group, chromenyl group, indolyl group, pyridyl group and quinolyl group; and groups having heterocyclic rings.

The alkyl group and the aryl group may have other functional groups such as hydroxyl group, halogen groups, nitro group, mercapto group, amino group, amide group, cyano group, carbonyl group, carboxyl group, acetyl group, acyl group, alkoxyl groups and sulfone group.

Among the fluorinating agents represented by general formula (I), compounds represented by general formula (I) in which Y represents nitrogen atom, $R^0$ represents 3-methylphenyl group or 2-methoxyphenyl group, and $R^1$ and $R^2$ represent ethyl group are preferable. Among these compounds, N,N-diethyl-α,α-difluoro(3-methyl)benzylamine and N,N-diethyl-α,α-difluoro(2-methoxy)benzylamine, which are compounds represented by general formula (I) in which $R^0$ represents 3-methylphenyl group or 2-methoxyphenyl group, and $R^1$ and $R^2$ represent ethyl group, are more preferable since the compounds exhibit the excellent heat stability such that the compounds are stable at a high temperature of 150° C. or higher.

It is preferable that the fluorinating agent represented by general formula (I) is used in an amount of 1 mole or more per 1 mole of the functional group in the substrate taking part in the reaction. The reaction may be allowed to proceed while the fluorinating agent is used in an excess amount or in an amount less than the stoichiometry.

The fluorination can be conducted in accordance with a batch process, a semi-batch process or a continuous process. The fluorination can be conducted in accordance with the conventional thermal reaction or under irradiation with microwave and/or electromagnetic wave having a wavelength around the microwave region.

The reaction can be safely performed when the temperature of the reaction is lower than the so-called runaway temperature under heating (the temperature at which the heat generation starts in the ARC test). It is preferable that the fluorination is conducted at 200° C. or lower and more preferably at a temperature in the range of the room temperature to 150° C. When the thermal reaction is conducted, the fluorination is conducted at a temperature lower than the runaway temperature under heating.

When the fluorination is conducted under irradiation with microwave or electromagnetic wave having a wavelength around the microwave region, in general, it is preferable that microwave having a frequency of 1 to 30 GHz is used. Electromagnetic wave having a frequency outside the above range such as millimeter wave having a frequency greater than 30 GHz and 300 GHz or smaller and electromagnetic wave having a frequency in the range of 0.3 GHz or greater and smaller than 1 GHz can also be used. The electromagnetic wave can be applied continuously or intermittently while the temperature is adjusted. For example, a conventional reactor for batch reactions is covered with a shield so that the microwave does not leak, and microwave is applied to the reactor. For this purpose, a commercial microwave oven is advantageously used, and a commercial oven for chemical synthesis may be used. The output of the magnetron tube for generation of microwave used for the reaction and the intensity of the irradiation are not particularly limited except the legal restrictions. An easily available tube having an output of 200 to 6,000 W is preferable. A plurality of tubes may be used in combination when a greater output is necessary. It is preferable that the intensity of the irradiation with microwave is, in general, 20 W/cm² or greater and more preferably 100 W/cm² or greater.

It is preferable that the time of the reaction is in the range of 10 to 360 minutes when the thermal reaction is conducted. When the reaction is conducted under irradiation of microwave and/or electromagnetic wave having a wavelength around the microwave region, in general, the time of the reaction is shorter than that in the thermal reaction. It is preferable that the time of the irradiation is 0.1 to 200 minutes, more preferably 0.1 to 60 minutes and most preferably 1 to 30 minutes although the time of the irradiation is different depending on the type of the substrate. In a pretreatment such as drying and in the fluorination, microwave may be applied for 3 hours or longer, where necessary. As for the temperature of the reaction, the reaction may be conducted at a temperature in a range such that the substrate, the fluorinating agent and the reaction products are stable. In general, a temperature in the range of the room temperature of about 25° C. to 200° C. is preferable. However, the reaction may be conducted at a temperature lower than the room temperature or higher than 200° C.

For making the fluorination proceed, it is not necessary that a solvent is used. A solvent may be used for conducting the stirring sufficiently or preventing elevation of the temperature. Examples of the preferable solvent include aliphatic hydrocarbons, aromatic hydrocarbons, halogenated hydrocarbons, aromatic halogenated hydrocarbons, nitriles and ethers which are inter to the substrate, the fluorinating agent and the reaction products. A suitable combination of the solvents may be used.

When the irradiation with microwave is completed, the reaction product may be separated after treatments such as post treatments, extraction, distillation and filtration similarly to the treatments in the ordinary thermal reaction.

When the reaction is conducted using the fluorinating agent represented by general formula (I) exhibiting the excellent heat stability in accordance with the thermal reaction or under irradiation with microwave and/or electromagnetic wave having a wavelength around the microwave region, a specific portion of a saccharide can be fluorinated selectively and easily without affecting the protective group in the wide range of the temperature which is difficult in conventional reactions.

The above method of fluorination comprising conducting the reaction under irradiation with microwave and/or electromagnetic wave having a wavelength around the microwave region can be applied to fluorination of substrates other than saccharides using a fluorinating agent other than the fluorinating agent represented by general formula (I).

For example, in the method of fluorination under irradiation with microwave and/or electromagnetic wave having a wavelength around the microwave region, a fluorinating agent represented by general formula (II):

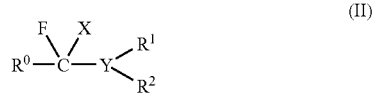

(II)

may be used.

In general formula (II), X represents hydrogen atom or a halogen atom, and R⁰, R¹ and R² and Y are as defined for general formula (I).

As the preferable fluorinating agent, a fluorinating agent represented by general formula (III):

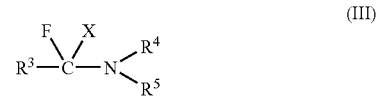

(III)

can also be used.

In general formula (III), R³, R⁴ and R⁵ each independently represent an alkyl or aryl group which may have substituents, and two or three of the groups represented by R³, R⁴ and R⁵ may be bonded to each other to form a ring structure. Examples of the alkyl group and the aryl group represented by R³, R⁴ and R⁵ include the groups described as the examples of the alkyl groups and the aryl groups represented by R⁰, R¹ and R³ in general formula (I).

In general formula (III), X represents hydrogen atom or a halogen atom such as fluorine atom, chlorine atom, bromine atom and iodine atom.

It is preferable that, in general formula (III) representing the fluorinating agent, R³ represents an aryl group which may have substituents, X represents fluorine atom, and R⁴ and R⁵ represent an alkyl group or aryl group having 1 to 32 carbon atoms which may have substituents.

Examples of the compound represented by general formula (III) include alkylfluoroamines and arylfluoroamines. Examples of the compound represented by general formula (III) in which R⁴ and R⁵ represent ethyl group include N,N-diethyl-α,α-difluorobenzylamine, N,N-diethyl-α,α-difluoro(2-methyl)benzylamine, N,N-diethyl-α,α-difluoro-(3-methyl)benzylamine, N,N-diethyl-α,α-difluoro(4-methyl)benzylamine, N,N-diethyl-α,α-difluoro(2-methoxy)benzylamine, N,N-diethyl-α,α-difluoro(4-phenyl)benzylamine, N,N-diethyl-α,α-difluorocylcohexylmethylamine, N,N-diethyl-α,α-difluoropyridylmethylamine and N,N-diethyl-α,α-difluorocyclohexylmethylamine.

Among the compounds represented by general formula (III), aromatic fluoroamines such as N,N-diethyl-α,α-difluoro(3-methyl)-benzylamine, N,N-diisopropyl-α,α-difluoro(3-methyl)benzylamine, N,N-diethyl-α,α-difluoro(2-methoxy)benzylamine, N,N-diisopropyl-α,α-difluoro-(2-methoxy)benzylamine and N,N-di-n-butyl-α,α-difluoro(2-methoxy)-benzylamine are preferable due to the excellent heat stability.

The substrates which can be fluorinated with the fluorinating agent represented by general formula (III) are organic compounds, polymers and inorganic compounds. The substrates are so numerous that it is difficult that examples corresponding to the entire substrates are shown. In general, the substrate is an organic compound having oxygen atom, nitrogen atom or sulfur atom. Examples of the organic compound include primary, secondary and tertiary alcohols having isolated hydroxyl groups as the functional groups; polyols having a plurality of hydroxyl groups such as 1,2-diols having adjacent hydroxyl groups, 1,3-diols and other polyols; thiols; compounds having carbonyl group or carboxyl group such as aldehydes, ketones, carboxylic acids, hydroxycarboxylic acid, esters of carboxylic acids and lactones; aromatic compounds exhibiting an increased nucleophilicity due to the presence of an electron-attracting group such as cyanohydrins, sulfonic acids, esters of sulfonic acids, thiocarboxylic acids, esters of thiocarboxylic acids and dinitrobenzenes; aromatic diazonium salts; heterocyclic compounds; saccharides such as monosaccharides, glycoxides, anhydrides of monosaccharides, oligosaccharides and polysaccharides; hydrocarbons having a cage shape such as fullerenes; and epoxides such as ethylene oxide and epichlorohydrin. Specific examples of the substrate include ethanol, propyl alcohol, butyl alcohol, heptanol, octanol, benzyl alcohol, phenetyl alcohol, nitrophenol, cyclohexanol, adamantanol, cholesterol, epiandrostrone, ethylene glycol, cyclohexanediol, glycerol, propylene oxide, alkyloxiranes, benzaldehyde, alkylbenzaldehydes, acetophenone, benzophenone, cyclopentanone, cyclohexanone, indanone, mandelonitrile, γ-butyrolactone, mevalonolactone, benzenesulfonic acid, naphthalene-sulfonic acid, thiobenzoic acid, methyl thiobenzoate, dinitrochlorobenzene, α-glucopyranose, β-D-fructofuranose, α-D-xylohexopyranose-4-urose, β-D-glucobinalronic acid and fullerenol. Examples of the specific compound providing a greater added value include 2-hydroxymethyl-saccharine as the raw material of 2-saccharinylmethylarylcarboxylates useful as the inhibitor for proteolysis enzymes, 2,3-di(4-pyridyl)-4-methylthiophene-3-carboaldehyde as an intermediate for pyridylthiophene used for curing diseases occurring via cytokine, dinucleotides and oligonucleotides used as the drug for curing diseases caused by viruses such as herpes, and 7β-carboxymethyl-4-aza-5α-cholestanone used as a raw material for the inhibitor for 5α-reductase.

Of course, the substrate used for fluorination using the fluorinating agent represented by general formula (III) is not limited to the compounds shown as the examples. Among the substrates, compounds having hydroxyl group, saccharides, compounds having carbonyl group or carboxyl group and epoxides are preferable. Among the compounds having hydroxyl group, compounds having adjacent hydroxyl groups are more preferable.

The procedures for fluorination using the fluorinating agent represented by general formula (III) under irradiation with microwave and/or electromagnetic wave having a wavelength around the microwave region are approximately the same as those for fluorination using the fluorinating agent represented by general formula (I) under irradiation with microwave and/or electromagnetic wave having a wavelength around the microwave region. The temperature of the reaction can be selected in a range such that the substrate, the fluorinating agent and the reaction products are stable. In general, a temperature in the range of the room temperature of about 25° C. to 200° C. is preferable. However, the reaction may be conducted at a temperature lower than the room temperature or higher than 200° C.

When the fluorinating agent represented by general formula (I) in which Y represents nitrogen atom or when the fluorinating agent represented by general formula (III) is used, the fluorinating agent can be recovered as the corresponding amide after the fluorination has been completed, and a process for fluorination allowing recycling of the materials can be constructed easily.

In accordance with the method of fluorination using the fluorinating agent represented by general formula (III) under irradiation with microwave and/or electromagnetic wave having a wavelength around the microwave region, the above substrate can be fluorinated efficiently in a short time safely with the excellent selectivity.

The method of fluorination under irradiation with microwave and/or electromagnetic wave having a wavelength around the microwave region can be applied to fluorination using a complex compound comprising HF and a base as the fluorinating agent.

Examples of the complex compound comprising HF and a base used as the fluorinating agent include alkylamine-HF complex compounds, melamine-HF complex compounds and pyridine-HF complex compounds. Among these complex compounds, the triethylamine-nHF complex compounds (in general, n represents an integer) are preferable, and the triethylamine-3HF complex compound is more preferable due to the easiness of handling since the compound can be distilled and glass vessels can be used due to the absence of the corrosive property.

When the complex compound of HF and a base is used as the fluorinating agent, an agent accelerating the reaction may be used in combination with the fluorinating agent to accelerate the reaction. As the agent accelerating the reaction, NBS (N-bromosuccinimide), DBH (1,3-dibromo-5,5-dimethylhidantoin) and sulfur chloride are used for the gem-difluorination of 1,3-dithiane, and sulfuryl compounds are used in combination with the complex compound of HF and a base for obtaining halofluorides or fluorosulfenyl compounds from olefins and alkynes.

Examples of the substrate used in the method of fluorination using the complex compound of HF and a base as the fluorinating agent under irradiation with microwave and/or electromagnetic wave having a wavelength around the microwave region include compounds having hydrogen atom activated by a substituent at the a position, the Deposition or the γ-position, silyl ether compounds, compounds having an unsaturated group, hydroxyl group, a halogeno group, amino group, diazo group, triazeno group or isocyano group as the functional group, and cyclic compounds having three-membered or greater ring which may have heteroatoms.

The above substrates are compounds which can take part in reactions such as conversion of functional groups into fluorine, ring-opening fluorination of cyclic compounds, gem-difluorination of 1,3-dithiolane and hydrazone, gem-trifluorination of ortho-thioesters, oxidative fluorination, reductive fluorination and reaction of removing the protective group of silyl ethers. Examples of the conversion of functional groups into fluorine include the halogen-fluorine exchange with halogen compounds, formation of halofluorides, fluorosulfenyl compounds and nitrofluoro compounds from unsaturated groups in olefins and alkynes, fluorination of hydroxyl groups in alcohols and saccharides and fluorination of amino group, diazo group, triazeno group and isocyano group with removal of diazo group.

Specific examples of the above substrate include cyclic compounds which may have heteroatoms such as cyclopropane, cyclobutane, cyclopentane, cyclobutene, cylopentene, cyclohexene, cycloheptene, cyclooctene, cyclodecene, cyclododecene, butene, 2,3-dimethylbutene, methylenecyclohexene, 5-α-cholest-2-ene, ethylene oxide, propylene oxide, oxetane, oxorane, cyclohexene oxide, cyclooctene oxide, cyclodecene oxide, cyclododecene oxide, alkyloxiranes, styrene oxide, norbornene oxide, aziridine, azirine, thiirane, azethidine, azolidine, thiazolidine, 1,3-dithiane; aromatic compounds, aromatic diazonium salts and heterocyclic compounds exhibiting increased nucleophilicity due to the presence of an electron-attracting group such as indanone, cyclopentanone, γ-butyrolactone, mevalonolacotne, bromoacetone, benzenesulfonic acid, naphthalenesulfonic acid, thiobenzoic acid, methyl thiobenzoate, acrylic acid, methyl acrylate, methacrylic acid, methyl methacrylate and trichloropyrimidine; alcohols having hydroxyl group as the functional group and sugars such as monosaccharides, oligosaccharides and polysaccharides, examples of which include allyl alcohol, allyl veratrol, citroneral, α-D-glucopyranose, β-D-fructofuranose, α-D-xylohexopyranose-4-urose and β-D-glucobinalronic acid; compounds having unsaturated bonds such as propylene, butene, tolan and acetylenes; and hydrocarbons having a cage shape such as fullerenes. The above compounds may further have a plurality of other functional groups.

Examples of the other functional group include a single or a plurality of hydroxyl groups, thiol groups, formyl groups, carbonyl groups, carbonyloxyl groups, alkyloxycarbonyl groups, cyano groups, sulfonyl groups, alkylsulfonyl groups, sulfenyl groups, thiocarbonyl groups, nitro groups, amino groups and diazo groups, which may be primary, secondary or tertiary groups. The above method can be applied not only to organic compounds, but also to inorganic compounds, materials obtained by introducing the functional group on the surface of polymers and organic-inorganic hybrid materials obtained by introducing the functional group.

Of course, the substrate used for fluorination using the complex compound of HF and a base under irradiation with microwave and/or electromagnetic wave having a wavelength around the microwave region is not limited to the compounds shown as the examples. In the present method, saccharides and cyclic compounds having cyclopropane ring, oxirane ring, aziridine ring, azirine ring or 1,3-dithiane ring are preferable among these substrates.

The procedures for fluorination using the complex compound of HF and a base under irradiation with microwave and/or electromagnetic wave having a wavelength around the microwave region are approximately the same as those for fluorination using the fluorinating agent represented by general formula (I). The temperature of the reaction can be selected in a range such that the substrate, the fluorinating agent and the reaction products are stable. In general, a temperature in the range of the room temperature of about 25° C. to 300° C. is preferable. However, the reaction may be conducted while the temperature is controlled at a value lower than the room temperature or higher than 200° C. similarly to the ordinary thermal reaction.

When the complex compound of HF and a base is used as the fluorinating agent under irradiation with microwave and/or electromagnetic wave having a wavelength around the microwave region, the complex compound of HF and a base which is stable and causes practically no corrosion, such as the triethylamine-HF complex, can be used in various types of fluorination for various substrates, and the fluorinationi can be conducted efficiently in a short time under a milder condition than that of the thermal reaction. Examples of the above fluorination include the ring-opening fluorination of compounds having hydrogen atom activated by a substituent at the a position, the β-position or the γ-position, silyl ether compounds, compounds having an unsaturated group, hydroxyl group, a halogeno group, amino group or diazonium group as the functional group, and cyclic compounds having three-membered or greater ring which may have heteroatoms, formation of halofluorides or fluorosulfenyl compounds from unsaturated compounds, the halogen-fluorine exchange, fluorination with removal of diazo group, gem-difluorination of 1,3-dithioranes and hydrazones and the removal of the protective group of silyl ethers.

The present invention will be described more specifically with reference to examples in the following. However, the present invention is not limited to the examples.

A. Using the Fluorinating Agent Represented by General Formula (I)

<Synthesis of the Fluorinating Agent> a) N,N-Diethyl-α-chloro-meta-toluylamidium chloride

Into a three-necked flask (300 ml), a solution of carbon tetrachloride (125 g) containing oxalyl chloride (25 g; 0.197 moles) was placed under the atmosphere of nitrogen. While the flask was cooled with ice water and the solution was stirred, N,N-diethyl-meta-toluamide (45 g; 0.236 moles; referred to as DEET, hereinafter) was added dropwise over 20 minutes. After the addition was completed, the resultant mixture was kept at the same temperature for 10 minutes. After the temperature of the content was adjusted at 50° C., the reaction was allowed to proceed for 1 hour. Generation of a gas was observed during the reaction, and then white precipitates were formed. The formed white precipitates were separated by filtration, washed with carbon tetrachloride and n-hexane and dried, and N,N-diethyl-α-chloro-meta-toluylamidium chloride was obtained. The obtained N,N-diethyl-α-chloro-meta-toluylamidium chloride was heated slowly in a capillary tube (a sealed tube) to 200° C. No decomposition was observed, and the compound was thermally stable.

It was found that the obtained N,N-diethyl-α-chloro-meta-toluylamidium chloride had a melting point of 54.6° C. in accordance with the thermal analysis using TG-DTA.

b) N,N-Diethyl-α,α-difluoro(3-methyl)benzylamine

Into a three-necked flask (500 ml), N,N-diethyl-α-chloro-meta-toluylamidium chloride (25 g; 0.1 mole) prepared above, a spray dried product of potassium fluoride (manufactured by MORITA KAGAKU Co., Ltd.; 23.5 g; 0.4 moles) and acetonitrile (250 g) were placed, and the reaction was allowed to proceed at the reflux temperature of acetonitrile for 18 hours under the atmosphere of nitrogen. After the reaction was completed, the reaction mixture was cooled to the room temperature and filtered, and an acetonitrile solution containing a product of fluorine exchange with N,N-diethylchloro-meta-toluylamidium chloride was obtained. The obtained solution was distilled using a rectifier of the rotating band type having a theoretical number of stage of 80, and 13 g of N,N-diethyl-α,α-difluoro(3-methyl)benzylamine (referred to as DEET-F, hereinafter) was obtained as a fraction at a temperature of 50 to 60° C. (the pressure: 2 mmHg, 260 Pa). The yield after the isolation by distillation was about 60% based on the amount of N,N-diethylchloro-meta-toluylamidium chloride.

The obtained fraction was a colorless transparent liquid and had the following properties.

(Heat Stability and the Runaway Temperature Under Heating)

A sample of the product was slowly heated in a capillary tube (a sealed tube) to 200° C. and kept at this temperature for 1 hour. No decomposition was observed, and the product was thermally stable. In the thermal analysis in which the temperature was raised to 400° C. at a rate of 10° C. per minute using an apparatus for the TG/DTA thermal analysis, heat generation started at 210° C., and a gradual decrease in the weight was observed. The peak temperature of the heat generation was 280° C. The temperature of the start of heat generation was 180° C. as measured in accordance with the method of measuring the runaway reaction of Japanese Industrial Standard (the ARC test) for evaluating the heat stability of a substance in the adiabatic condition.

(Content of Fluorine)

Calculated: 17.8% by weight; found: 17.6% by weight.

c) N,N-Diethyl-2-methoxybenzamide

Into a three-necked flask (200 ml), a toluene solution (56 g) containing diethylamine (25.80 g; 0.352 moles) was placed. While the flask was cooled with ice water and the solution was stirred, a toluene solution (30 g) of 2-methoxybenzoyl chloride (2.00 g; 0.117 moles) was added dropwise over 30 minutes. After the addition was completed, water was added to the resultant mixture, and diethylamine and diethylamine hydrochloride in excess amounts were removed. The obtained toluene layer was dehydrated with $MgSO_4$. Then, the solvent was removed by distillation, and a light yellow liquid was obtained (the obtained amount: 22.81 g; the yield: 94%).

d) Synthesis of N,N-diethyl-α-chloro(2-methoxyphenyl)amidium chloride

Into a three-necked flask (200 ml), a solution of carbon tetrachloride (54 g) containing oxalyl chloride (24.50 g; 0.193 mole) was placed under the atmosphere of nitrogen. To the resultant mixture, N,N-diethyl-2-methoxybenzamide (20.05 g; 0.0965 moles) was added dropwise over 20 minutes at the room temperature. After the addition was completed, the temperature of the content was adjusted at 50° C., and the reaction was allowed to proceed for 5 hours. Generation of a gas was observed during the reaction, and then the reaction mixture was separated into two layers. After the reaction was completed, the solvent was removed by distillation. When the resultant product was left standing, a charcoal brown solid was obtained. The obtained solid was washed with carbon tetrachloride and n-hexane and dried, and N,N-diethyl-α-chloro(2-methoxyphenyl)amidium chloride was obtained (the obtained amount: 21.40 g; the yield: 80%).

To confirm the ability of chlorination of the obtained N,N-diethyl-α-chloro(2-methoxyphenyl)amidium chloride, the reaction with benzyl alcohol was conducted in a glove box. Into a test tube, N,N-diethyl-α-chloro(2-methoxyphenyl)amidium chloride (0.20 g; 0.465 moles), benzyl alcohol (0.11 g; 1.017 moles) and acetonitrile (1.10 g) were placed, and the reaction was allowed to proceed at the room temperature for 4 hours. As the result of analysis of the reaction fluid in accordance with GC, the formation of benzyl chloride was confirmed.

e) N,N-Diethyl-α,α-difluoro(2-methoxy)benzylamine

In a glove box, N,N-diethyl-α-chloro(2-methoxyphenyl) amidium chloride prepared above (20.00 g; 0.0725 moles), potassium fluoride (manufactured by MORITA KAGAKU SPRAY DRY Co., Ltd.; 17.72 g; 0.3052 moles) and acetonitrile (200 g) were placed into a three-necked flask (100 ml). Under the atmosphere of nitrogen, a condenser and an electromagnetic stirrer were attached to the flask, and the reaction was allowed to proceed at 80° C. for 20 hours. After the reaction was completed, the reaction mixture was cooled to the room temperature and filtered in the glove box, and an acetonitrile solution containing a product of fluorine exchange with N,N-diethyl-α-chloro(2-methoxyphenyl) amidium chloride was obtained.

This solution was distilled using a rectifier of the rotating band type having a theoretical number of stage of 80, and N,N-diethyl-α,α-difluoro(2-methoxy)benzylamine (9.86 g; the yield: 55%) was obtained as a fraction at a temperature of 77 to 80° C. under a pressure of 2 mm Hg (260 Pa).

The obtained fraction was colorless transparent liquid and had the following properties.

(Heat Stability and the Runaway Temperature)

A sample of the product was slowly heated in a capillary tube (a sealed tube) to 200° C. and kept at this temperature for 1 hour. No decomposition was observed, and the product was thermally stable. In the thermal analysis in which the temperature was raised to 400° C. at a rate of 10° C. per minute using an apparatus for the TG/DTA thermal analysis, heat generation started at 20 to 210° C., and a gradual decrease in the weight was observed. The peak temperature of the heat generation was 255° C. The temperature of the start of heat generation was 159° C. as measured in accordance with the method of measuring the runaway reaction of Japanese Industrial Standard (the ARC test) for evaluating the heat stability of a substance in the adiabatic condition.

EXAMPLE 1

Fluorination of methyl 2,3-O-isopropylidene-β-D-ribo-furanoside

A 100 ml glass reactor equipped with a stirrer and a condenser and coated with a fluororesin was used. Into the reactor, methyl 2,3-O-isopropylidene-β-D-ribofuranoside (10 mmole) as the substrate, N,N-diethyl-α,α-difluoro(3-methyl)benzylamine (12 mmole; 2.56 g) as the fluorinating agent and 20 ml of heptane were placed. While the resultant mixture was stirred, the temperature was raised from the room temperature to 100° C., and the reaction was allowed to proceed for 60 minutes. After the reaction was completed, 50 ml of water was added to the fluid formed by the reaction, and the resultant mixture was treated by extraction twice with 20 ml of dichloromethane. The extract was dried with magnesium sulfate, filtered and distilled under a reduced pressure, and a product was obtained. The product was identified in accordance with IR, NMR and the mass analysis and quantitatively analyzed in accordance with the gas chromatography or the liquid chromatography. The yield of methyl 2,3-O-isopropylidene-5-deoxy-5-fluoro-β-D-ribofuranoside as the product was 55%.

EXAMPLE 2

Fluorination of methyl 2,3-O-isopropylidene-β-D-ribo-furanoside

In a microwave oven in which uniform irradiation can be made by a distributor of the pyramid type (the width and the depth: 55 cm; the height: 70 cm; the output: 1 KW; the frequency: 2.45 GHz), a 100 ml glass reactor equipped with a stirrer and a condenser and coated with a fluororesin was placed. Into the reactor, methyl 2,3-O-isopropylidene-β-D-ribofuranoside (10 mmole; 2.04 g) as the substrate and N,N-diethyl-α,α-difluoro(3-methyl)benzylamine (12 mmole; 2.56 g) as the fluorinating agent were placed. While the resultant mixture was stirred at the room temperature, the mixture was irradiated with microwave for 10 minutes. After the irradiation was completed, the same treatments as those conducted in Example 1 were conducted, and methyl 2,3-

O-isopropylidene-5-deoxy-5-fluoro-β-D-ribofuranoside as the object product was obtained at a yield of 65%. As a byproduct, 2,3-O-isopropylidene-5-O-methyl-β-D-ribofuranosyl fluoride was obtained at a yield of 20%.

COMPARATIVE EXAMPLE 1

Fluorination of methyl 2,3-O-isopropylidene-β-D-ribo-furanoside

Into 20 ml of dried dichloromethane, methyl 2,3-O-isopropylidene-β-D-ribofuranoside (10 mmole) as the substrate was dissolved. While the solution was stirred under the nitrogen stream, N,N-diethylaminosulfur trifluoride (DAST, 10 mmole) was slowly added dropwise. After the addition was completed, the reaction was allowed to proceed for 15 minutes. Water in an amount of 50 ml was poured into the obtained reaction fluid. After the resultant mixture was separated into two layers, the organic layer was dried with magnesium sulfate and treated for separation in accordance with the chromatography. 2,3-O-Isopropylidene-5-deoxy-β-D-furanosyl fluoride was obtained as the product of rearrangement at a yield of 55%. However, methyl 2,3-O-isopropylidene-5-deoxy-5-fluoro-β-D-ribofuranoside of the object compound was not obtained at all.

EXAMPLE 3

Fluorination of ethyl 2,3-O-diisopropylidene-β-D-ribo-furanoside

The same procedures as those conducted in Example 2 were conducted except that ethyl 2,3-O-isopropylidene-β-D-ribofuranoside (10 mmole) as the substrate and N,N-diethyl-α,α-difluoro(3-methyl)-benzylamine (20 mmole) as the fluorinating agent were used. As the products, ethyl 2,3-O-isopropylidene-5-deoxy-5-fluoro-β-D-ribofuranoside was obtained at a yield of 55%, and 2,3-O-isopropylidene-5-O-ethyl-β-D-furanosyl fluoride was obtained at a yield of 21%.

EXAMPLE 4

Fluorination of isopropyl 2,3-O-isopropylidene-β-D-ribo-furanoside

The same procedures as those conducted in Example 3 were conducted except that isopropyl 2,3-O-isopropylidene-β-D-ribofuranoside (10 mmole) was used as the substrate. As the products, isopropyl 2,3-O-isopropylidene-5-deoxy-5-fluoro-β-D-ribofuranoside was obtained at a yield of 62%, and 2,3-O-isopropylidene-5-O-isopropyl-β-D-furanosyl fluoride was obtained at a yield of 22%.

EXAMPLE 5

Fluorination of 2',3'-O-isopropylideneuridine

The same procedures as those conducted in Example 3 were conducted except that 2',3'-O-isopropylideneuridine (10 mmole) was used as the substrate. As the product, 2',3'-O-isopropylidene-5'-deoxy-5'-fluorouridine was obtained at a yield of 55%.

EXAMPLE 6

Fluorination of 1,2,3,4-di-O-isopropylidene-α-D-galacto-pyranose

The same procedures as those conducted in Example 3 were conducted except that N,N-diethyl-α,α-difluoro(3-methyl)benzylamine (20 mmole) was used as the substrate. As the product, 1,2,3,4-di-O-isopropylidene-6-deoxy-6-fluoro-α-D-galactopyranose was obtained at a yield of 75%.

EXAMPLE 7

Fluorination of α-D-ribofuranose 1,3,5-tribenzoate

Into a pressure resistant vessel (200 ml) of the closed type which was made of Teflon and attached with a fiber optic temperature sensor, a stirrer rod, α-D-ribofuranose 1,3,5-tribenzoate (11 mmole; 5.1 g) and 50 ml of acetonitrile were placed. To the resultant mixture, N,N-diethyl-α,α-difluoro (3-methyl)benzylamine (23.2 mmole; 49.5 g) was slowly added under a nitrogen atmosphere. The temperature was then raised to 200° C. at a rate of 20° C./min under stirring, and the reaction was allowed to proceed for 20 minutes. After the reaction was completed, the reaction product was poured into 200 ml of ice water, and the organic layer was separated. The aqueous layer was treated by extraction with 50 ml of acetonitrile. The obtained two organic layers were combined, washed with pure water, dried with magnesium sulfate and then filtered. The obtained organic solution was concentrated using an evaporator, and the concentrated solution was analyzed in accordance with the liquid chromatography. As the result, 2.8 g (the yield: 55%) of 2-deoxy-2-fluoro-α-D-ribofuranose 1,3,5-tribenzoate of the object compound was obtained.

EXAMPLE 8

Fluorination of 2,3,5,6-di-O-isopropylidene-D-mannofuranose

The same procedures as those conducted in Example 1 were conducted except that 2,3,5,6-di-O-isopropylidene-D-mannofuranose (10 mmole) was used as the substrate, and the reaction was allowed to proceed at the room temperature for 1 hour. As the product, 2,3,5,6-diisopropylidene-D-mannofuranosyl fluoride was obtained at a yield of 94% without removal of the acetonide of the protective group at all.

COMPARATIVE EXAMPLE 2

Fluorination of 2,3,5,6-di-O-isopropylidene-D-mannofuranose

The same procedures as those conducted in Example 8 were conducted except that HF (20 mmoles) was used as the fluorinating agent. As the result, the protective group was removed, and 2,3,5,6-di-O-isopropylidene-D-mannofuranosyl fluoride of the object compound was not obtained at all. The fluorination at the 1-position could not be achieved.

EXAMPLE 9

Fluorination of 2,3,4,5-tetra-O-acetyl-D-glucopyranose

The same procedures as those conducted in Example 1 were conducted except that 2,3,4,5-tetra-O-acetyl-D-glucopyranose (10 mmole) was used as the substrate, and the reaction was allowed to proceed at the room temperature for 1 hour in methylene chloride. As the product, 2,3,4,5-tetra-O-acetyl-D-glucopyranosyl fluoride was obtained at a yield of 84% without removal of the acetyl group of the protective group at all.

COMPARATIVE EXAMPLE 3

Fluorination of 2,3,4,5-tetra-O-acetyl-D-glucopyranose

The same procedures as those conducted in Example 9 were conducted except that HF (20 mmoles) was used as the fluorinating agent. As the result, the protective group was removed, and 2,3,4,5-tetra-O-acetyl-D-glucopyranosyl fluoride of the object compound was not obtained. The fluorination at the 1-position could not be achieved.

EXAMPLE 10

Fluorination of 2,3,4,5-tetra-O-acetyl-D-glucopyranose

The same procedures as those conducted in Example 2 were conducted except that 2,3,4,5-tetra-O-acetyl-D-glucopyranose (10 mmole) was used as the substrate. As the product, 2,3,4,5-tetra-O-acetyl-D-glucopyranosyl fluoride was obtained at a yield of 84% without removal of the acetyl group of the protective group at all.

EXAMPLE 11

Fluorination of α-D-ribofuranose 1,3,5-tribenzoate

The same procedures as those conducted in Example 7 were conducted except that α-D-ribofuranose 1,3,5-tribenzoate (11 mmole) was used as the substrate, N,N-diethyl-α,α-difluoro(2-methoxy)benzylamine (23.2 mmole) was used as the fluorinating agent, and the reaction was allowed to proceed at 120° C. for 30 minutes. As the product, 2-deoxy-2-fluoro-α-D-robofuranose 1,3,5-tribenzoate was obtained at a yield of 85%.

EXAMPLE 12

Fluorination of D-xylopyranose

The same procedures as those conducted in Example 9 were conducted except that D-xylopyranose (10 mmole) was used as the substrate, and a fluorination agent (80 mmole) was used. As the product, 2,3,4-tri-O-(3'-methylbenzoyl)-D-xylopyranosyl fluoride was obtained at a yield of 57%.

EXAMPLE 13

Fluorination of 1,2,3,4-di-O-isopropylidene-α-D-galactopyranose

The same procedures as those conducted in Example 6 were conducted except that N,N-diethyl-α,α-difluoro(2-methoxy)benzylamine (20 mmole) was used as the fluorinating agent, and the reaction was allowed to proceed at 120° C. for 48 hours without the irradiation with microwave. As the product, 1,2,3,4-di-O-isopropylidene-6-deoxy-6-fluoro-α-D-galactopyranosyl fluoride was obtained at a yield of 58%.

B. Using the Fluorinating Agent Represented by General Formula (III)

<Fluorination of a Primary Alcohol>

EXAMPLE 14

1-Dodecanol

In a microwave oven in which uniform irradiation can be made by a distributor of the pyramid type (the width and the depth: 55 cm; the height: 70 cm; the output: 1 KW; the frequency: 2.45 GHz), a 100 ml glass reactor equipped with a stirrer and a condenser and coated with a fluororesin was placed. Into the reactor, 1-dodecanol (10 mmole; 1.86 g) as the substrate and N,N-diethyl-α,α-difluoro(3-methyl)benzylamine (12 mmole; 2.25 g) as the fluorinating agent were placed. While the resultant mixture was stirred at the room temperature, the mixture was irradiated with microwave for 10 minutes. After the irradiation with microwave was completed, 50 ml of water was added to the fluid formed by the reaction, and the resultant mixture was treated by extraction twice with 20 ml of dichloromethane. The extract was dried with magnesium sulfate, filtered and distilled under a reduced temperature, and a product was obtained. The product was identified in accordance with IR, NMR and the mass analysis and quantitatively analyzed in accordance with the gas chromatography or the liquid chromatography. The yield of 1-fluorododecane as the product was found to be 93%.

COMPARATIVE EXAMPLE 4

1-Dodecanol

The reaction was conducted in accordance with the same procedures as those conducted in Example 14 except that the irradiation with microwave was not conducted. The yield of 1-fluorododecane was 45% when the reaction was allowed to proceed at a temperature of 110° C. for 10 minutes and 12% when the reaction was allowed to proceed at the room temperature for 17 hours.

EXAMPLE 15

10-Undecene-1-ol

In the same apparatus as that used in Example 14, 10-undecene-1-ol (10 mmole; 1.7 g) as the substrate and N,N-diethyl-α,α-difluoro(3-methyl)benzylamine (12 mmole; 2.56 g) as the fluorinating agent were added to heptane as the solvent. While the resultant mixture was stirred at the room temperature, the mixture was irradiated with microwave for 10 minutes. As the product, 1-fluoro-10-undecene was obtained at a yield of 91%.

EXAMPLE 16

Ethylene Glycol

The reaction was conducted in accordance with the same procedures as those conducted in Example 15 except that ethylene glycol (10 mmole) was used, and n-heptane of the solvent was not used. One of the two hydroxyl groups in ethylene glycol alone was fluorinated after the irradiation with microwave for 10 minutes. As the product, 2-((3-methyl)benzoyloxy)-1-fluoroethane was obtained at a yield of 83%.

<Fluorination of a Secondary Alcohol>

EXAMPLE 17 cis-Cyclohexane-1,2-diol

The reaction was conducted in accordance with the same procedures as those conducted in Example 16 except that cis-cyclohexane-1,2-diol (10 mmole) was used as the substrate. As the product, (trans)-1-fluoro-2-((3-methyl)benzoyloxy)cyclohexane was obtained at a yield of 89%.

EXAMPLE 18

Cyclododecanol

The reaction was conducted in accordance with the same procedures as those conducted in Example 16 except that cyclododecanol (10 mmole) was used as the substrate. As the product, fluorocyclododecane and cyclododecene were obtained at yields of 16% and 84%, respectively.

<Fluorination of a Tertiary Hydroxyl Group>

EXAMPLE 19

Methyl α-hydroxyisobutyrate

The reaction was conducted in accordance with the same procedures as those conducted in Example 16 except that methyl α-hydroxyisobutyrate (10 mmole) was used as the substrate. As the product, methyl α-fluoroisobutyrate was obtained at a yield of 93%.

COMPARATIVE EXAMPLE 5

Methyl α-hydroxyisobutyrate

A 100 ml glass reactor equipped with a stirrer and a condenser and coated with a fluororesin was used. Into the reactor, methyl α-hydroxyisobutyrate (10 mmole) as the substrate, N,N-diethyl-α,α-difluoro(3-methyl)benzylamine (12 mmole; 2.56 g) as the fluorinating agent and 20 ml of n-heptane as the solvent were placed. The reaction was allowed to proceed at 20° C. for 5 hours under stirring. The yield of methyl α-fluoroisobutyrate was 80%.

EXAMPLE 20

1-Adamantanol

The reaction was conducted in accordance with the same procedures as those conducted in Example 16 except that 1-adamantanol (10 mmole) was used as the substrate. As the product, 1-fluoro-adamantane was obtained at a yield of 96%.

COMPARATIVE EXAMPLE 6

1-Adamantanol

The reaction was conducted in accordance with the same procedures as those conducted in Comparative Example 4 using the same apparatus as that used in Comparative Example 4 except that 1-adamantanol (10 mmole) was used as the substrate. As the product obtained after the reaction at 20° C. for 5 hours under stirring, 1-fluoroadamantanol was obtained at a yield of 68%.

<Fluorination of an Epoxy Compound>

EXAMPLE 21

2-(n-Decyl)oxirane

The reaction was conducted in accordance with the same procedures as those conducted in Example 16 except that 2-(n-decyl)oxirane (10 mmole) was used as the substrate, dodecane was used as the solvent, and the irradiation with microwave was conducted for 30 minutes. As the product, 1,2-difluorododecane, i.e., a compound obtained by introduction of two fluorine atoms, was obtained at a yield of 65%.

<Fluorination of a Carbonyl Compound>

EXAMPLE 22

Benzaldehyde

The reaction was conducted in accordance with the same procedures as those conducted in Example 16 except that benzaldehyde (10 mmole) was used as the substrate. The yield of difluoromethylbenzene as the product was 86%.

EXAMPLE 23

Cyclohexanone

The reaction was conducted in accordance with the same procedures as those conducted in Example 16 except that cyclohexanone (10 mmole) was used as the substrate. As the products, difluorocyclohexane (the yield: 32%) and fluorocyclohexene (the yield: 58%) were obtained.

EXAMPLE 24

Benzoic Acid

The reaction was conducted in accordance with the same procedures as those conducted in Example 16 except that benzoic acid (10 mmole) was used as the substrate. The yield of benzoyl fluoride as the product was 99%.

COMPARATIVE EXAMPLE 7

Cyclohexanone

Using cyclohexanone (10 mmole) as the substrate and 10 mmole of 1,3-dimethyl-2,2-difluoroimidazolidine (DFI; manufactured by MITSUI KAGAKU KOGYO Co., Ltd.) as the fluorinating agent, the irradiation with microwave was conducted in accordance with the same procedures as those conducted in Example 16. However, a runaway reaction started immediately, and the reaction was stopped due to the danger. No object compound was obtained at all.

C. Using a Complex Compound of HF and a Base as the Fluorinating Agent

EXAMPLE 25

In a microwave oven in which uniform irradiation can be made by a distributor of the pyramid type (the width and the depth: 55 cm; the height: 70 cm; the output: 1 KW; the frequency: 2.46 GHz), a 5 ml reactor made of a fluororesin (PFA) and equipped with a reflux condenser was placed, and the fluorination was conducted.

Into the reactor, cyclohexene oxide (1 mmole; 0.1 g) as the substrate and triethylamine-3HF (0.6 mmole; 0.1 g) as the fluorinating agent were placed, and the resultant mixture was irradiated with microwave for 2 minutes without stirring. After the irradiation with microwave was completed, the fluid formed by the reaction was cooled to the room temperature, poured into 15 ml of water and treated by extraction twice with 15 ml of diethyl ether. The extract was neutralized with an aqueous solution of sodium hydrogencarbonate and dried by adding a suitable amount of anhydrous potassium carbonate. After the solvent was removed by distillation under a reduced pressure, the obtained product was purified in accordance with the column chromatography (hexane:$Et_2O$=1:1). As the product, trans-2-fluorocyclohexanol was obtained at a yield of 71% (the purity: 98% or greater).

COMPARATIVE EXAMPLE 8

The same procedures as those conducted in Example 25 were conducted except that the irradiation with microwave was not conducted, and the reaction was allowed to proceed at a temperature of 115° C. for 4 hours. The yield of trans-2-fluorocyclohexanol as the product was 61%.

EXAMPLE 26

Using the same apparatus as that used in Example 25, the same procedures as those conducted in Example 25 were conducted except that cyclododecene oxide (1 mole; 0.17 g; the ratio of the isomers=31:69) and $Et_3N$-3HF (0.6 moles; 0.1 g) were used, and the irradiation with microwave was conducted for 10 minutes. As the product, 2-fluorocyclododecanol was obtained at a yield of 76%.

COMPARATIVE EXAMPLE 9

The same procedures as those conducted in Example 26 were conducted except that the irradiation with microwave was not conducted, and the reaction was allowed to proceed at a temperature of 155° C. for 4 hours. The yield of 2-fluorocyclododecanol as the product was 54%.

EXAMPLE 27

Using the same apparatus as that used in Example 25, the same procedures as those conducted in Example 25 were conducted except that cyclooctene oxide (1 mole) and $Et_3N$-3HF (1 mole) were used, and the irradiation with microwave was conducted for 10 minutes. As the product, trans-2-fluorocyclohexanol was obtained at a yield of 68%.

COMPARATIVE EXAMPLE 10

The same procedures as those conducted in Example 27 were conducted except that the irradiation with microwave was not conducted. The yield of trans-2-fluorocyclooctanol as the product was 54%.

EXAMPLE 28

The same procedures as those conducted in Example 25 were conducted except that cyclododecane-1,4,8-triene monoxide (1 mole) as the substrate and $Et_3N$-3HF (1 mole) were used, and the irradiation with microwave was conducted for 2 minutes. As the product, 2-fluorocyclododecane-6,10-diene-1-ol was obtained at a yield of 78%.

COMPARATIVE EXAMPLE 11

The same procedures as those conducted in Example 28 were conducted except that the irradiation with microwave was not conducted, and the reaction was allowed to proceed at a temperature of 155° C. for 4 hours. The yield of 2-fluorocyclododecane-6,10-diene-1-ol as the product was 51%.

EXAMPLES 29 TO 36 AND COMPARATIVE EXAMPLES 12 TO 19

Using the same apparatus as that used in Example 25, the fluorination under irradiation with microwave (Examples) and the fluorination in accordance with the thermal reaction (Comparative Examples) were compared using the substrates and the fluorinating agents shown in Table 1. The results are shown in Table 1.

EXAMPLE 37

The same procedures as those conducted in Example 25 were conducted except that 3-phenylpropyl methyl sulfonate (1 mmole) and $Et_3N$-3HF (1.2 mmole) were placed in a 10 ml reactor made of PFA, and the irradiation with microwave was conducted for 2 minutes. As the product, 1-fluoro-3-phenylpropane was obtained at a yield of 80%.

COMPARATIVE EXAMPLE 20

The reaction was conducted in accordance with the same procedures as those conducted in Example 37 except that the reaction of 3-phenylpropyl methyl sulfonate (1 mmole) and Et$_3$N-3HF (10 mmole) was allowed to proceed at 80° C. for 100 hours in an acetonitrile solvent, and the yield of the product was examined. The change in the yield of 1-fluoro-3-methylpropane with time was as follows:

| | |
|---|---|
| The yield after 10 hours: | 12% |
| The yield after 20 hours: | 20% |
| The yield after 38 hours: | 44% |
| The yield after 54 hours: | 74% |
| The yield after 79 hours: | 80% |
| The yield after 100 hours: | 80% |

TABLE 1

(Reaction): substrate to product

| Example and Comparative Example | Fluorinating agent (reaction agent) | Temperature (° C.) | Time (min) | Yield (%) |
|---|---|---|---|---|
| (Hydrofluorination): 2,3-dimethyl-2-butene to 2-fluoro-2,3-dimethylbutane | | | | |
| Example 29 | triethylamine-3HF | room temp. | 5 | 77 |
| Comparative Example 12 | triethylamine-3HF | 100 | 60 | 72 |
| (Halofluorination): cyclododecene to 1-bromo-2-fluorododecane | | | | |
| Example 30 | triethylamine-3HF (NBS) | room temp. | 5 | 98 |
| Comparative Example 13 | triethylamine-3HF (NBS) | room temp. | 60 | 95 |
| (Halogen-fluorine exchange): 2,4,6-trichloro-5-methylpyrimidine to 2,4,6-trifluoro-5-methylpyrimidine | | | | |
| Example 31 | triethylamine-3HF | room temp. | 5 | 94 |
| Comparative Example 14 | triethylamine-3HF | 60 | 360 | 91 |
| (Fluorination with removal of diazo group): benzene diazoniumtetrafluoroborate to fluorobenzene | | | | |
| Example 32 | triethylamine-3HF | room temp. | 10 | 96 |
| Comparative Example 15 | triethylamine-3HF | 40 | 480 | 76 |
| (Removal of protective group of a silyl ether): 1,3-butanediol 1-t-butyldiphenylsiyl ether to 1,3-butanediol | | | | |
| Example 33 | triethylamine-3HF | room temp. | 5 | 89 |
| Comparative Example 16 | triethylamine-3HF | 80 | 480 | 82 |
| (Reductive fluorination): 2-adamantane to 2-fluoroadamantane | | | | |
| Example 34 | pyridine-3HF (triethylsilane) | room temp. | 5 | 78 |
| Comparative Example 17 | pyridine-3HF (triethylsilane) | 60 | 60 | 68 |
| (Fluorination of saccharide): β-D-glucopyranosyl bromide tetraacetate to β-D-glucopyranosyl fluoride tetraacetate | | | | |
| Example 35 | triethylamine-3HF | room temp. | 5 | 84 |
| Comparative Example 18 | triethylamine-3HF | 60 | 120 | 68 |
| (Fluorination of saccharide): β-D-glucopyranosyl tetraacetate to β-D-glucopyranosilyl fluoride triacetate | | | | |
| Example 36 | triethylamine-3HF | room temp. | 10 | 61 |
| Comparative Example 19 | triethylamine-3HF | room temp. | 180 | 0 |

INDUSTRIAL APPLICABILITY

In accordance with the present invention, the fluorination of various substrates which are hardly fluorinated in accordance with the conventional technology can proceed highly selectively, efficiently in a short time and safely. The substrates are, for example, saccharides useful as the functional chemical such as materials for drugs, cosmetics and healthy foods, compounds having hydrogen atom activated by a substituent at the α position, the β-position or the γ-position, silyl ether compounds, compounds having an unsaturated group, hydroxyl group, a halogeno group, amino group, diazo group, triazeno group or isocyano group as the functional group, and cyclic compounds having three-membered or greater ring which may have heteroatoms.

The invention claimed is:

1. A method of fluorination which comprises fluorinating a monosaccharide or monosaccharide bonded to a base of a nucleic acid using a fluorinating agent represented by general formula (I):

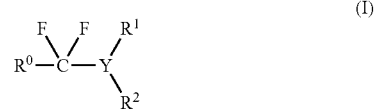

wherein Y represents nitrogen atom, $R^1$ and $R^2$ represent hydrogen atom or an alkyl group having 1 to 4 carbon atoms, and $R^1$ and $R^2$ may be bonded to each other to form a ring, and $R^0$ represents a benzene ring or a pyridine ring, which has one or two substituents selected from the group consisting of alkyl group having 1 to 2 carbon atoms, halogen atom, methoxy group, amino group and nitro group, which may be the same as or different from each other.

2. A method of fluorination according to claim 1, wherein, in general formula (I), Y represents nitrogen atom, $R^0$ represents 3-methyphenyl group or 2-methoxyphenyl group, and $R^1$ and $R^2$ represent ethyl group.

3. A method of fluorination according to claim 1, wherein the monosaccharide or monosaccharide bonded to a base of a nucleic acid is fluorinated by a thermal reaction.

4. A method of fluorination which comprises fluorinating a monosaccharide or monosaccharide bonded to a base of a nucleic acid by bringing the monosaccharide or monosaccharide bonded to a base of a nucleic acid and a fluorinating agent represented by the general formula (II):

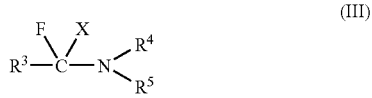
(III)

wherein Y represents nitrogen atom or phosphorus atom, X represents hydrogen or halogen atom, $R^0$, $R^1$ and $R^2$ represent hydrogen atom or an alkyl or aryl group which may have substituents, the atom and the groups represented by $R^0$, $R^1$ and $R^2$ may be a same with or different from each other, and two or three of the groups represented by $R^0$, $R^1$ and $R^2$ may be bonded to each other to form a ring into reaction with each other under irradiation with at least one of microwave and electromagnetic wave having a wavelength around a microwave region.

5. A method of fluorination according to claim 4, wherein the monosaccharide or monosaccharide bonded to a base of a nucleic acid is fluorinated by bringing the monosaccharide or monosaccharide bonded to a base of a nucleic acid and the fluorinating agent represented by general formula (I) into reaction with each other under irradiation with microwave having a frequency of 1 to 30 GHz.

6. A method of fluorination according to claim 4, wherein the fluorinating agent is a compound represented by general formula (III):

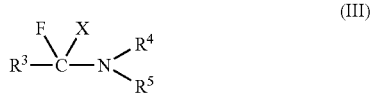
(III)

wherein $R^3$, $R^4$, and $R^5$ each independently represent an alkyl or aryl group which may have substituents, X represents hydrogen atom or a halogen atom, and two or three of the groups represented by $R^3$, $R^4$, and $R^5$ may be bonded to each other to form a cyclic structure.

7. A method of fluorination according to claim 6, wherein, in general formula (III), $R^3$ represents an aryl group which may have substituents, X represents fluorine atom, and $R^4$ and $R^5$ represent an alkyl or aryl group having 1 to 32 carbon atoms which may have substituents.

8. A method of fluorination according to claim 4, wherein the fluorinating agent is a compound represented by general formula (II) in which X represents fluorine atom.

9. A method of fluorination according to claim 4, wherein the fluorinating agent is a compound represented by general formula (II) in which X represents fluorine atom, Y represents nitrogen atom, R° represents 3-methylphenyl group or 2-methoxyphenyl group, and $R^1$ and $R^2$ represent ethyl group.

10. A method of fluorination according to claim 4, wherein the fluorination is conducted in a presence of an agent accelerating a reaction.

11. The method of fluorination according to claim 1, wherein the monosaccharide is selected from the group consisting of glucose, fucose, N-acetylglucosamine, N-acetylgalactosamine, N-acetylneuraminic acid, erythrose, threose, ribose, arabinose, xylose, arose, lyxose, altrose, mannose, gulose, dose, galactose, talose, psicose, furctose, sorbose, tagatose, hexaenose, apiose, and a deoxy sugar, an amino sugar, a thio sugar, a condensed sugar and an anhydride of the monosaccharide, and the monosaccharide bonded to a base of a nucleic acid is selected from the group consisting of a nucleoside, an oligonucleoside, ribonucleic acid and deoxyribonucleic acid.

* * * * *